United States Patent
Otsuka et al.

(10) Patent No.: US 6,191,326 B1
(45) Date of Patent: Feb. 20, 2001

(54) PROCESS FOR PREPARING 1,1,1,2,3,3,3-HEPTAFLUOROPROPANE

(75) Inventors: Tatsuya Otsuka; Hirokazu Aoyama, both of Settsu (JP)

(73) Assignee: Daikin Industries, Inc., Osaka-fu (JP)

( * ) Notice: Under 35 U.S.C. 154(b), the term of this patent shall be extended for 0 days.

(21) Appl. No.: 09/389,384

(22) Filed: Sep. 3, 1999

(30) Foreign Application Priority Data

Sep. 3, 1998 (JP) .................................................. 10-249835

(51) Int. Cl.⁷ .................................................. C07C 19/08
(52) U.S. Cl. .......................................... 570/142; 570/134
(58) Field of Search ..................... 570/134, 142

(56) References Cited

U.S. PATENT DOCUMENTS 3,399,179 * 8/1968 Grakauskas .......................... 260/92.1
5,573,654   11/1996 Cheburkov et al. .

FOREIGN PATENT DOCUMENTS

| 8-24362 | 1/1996 | (JP) . |
| 8-325179 | 12/1996 | (JP) . |
| 10-53543 | 2/1998 | (JP) . |
| WO98/28247 | 7/1998 | (WO) . |

OTHER PUBLICATIONS

V. Grakauskas, *Aqueous Fluorination Of Carboxylic Acid Salts*, Journal of Organic Chemistry, vol. 34, No. 8, Aug. 1969, pp. 2446–2450.

* cited by examiner

*Primary Examiner*—Johann Richter
*Assistant Examiner*—J. Parsa
(74) *Attorney, Agent, or Firm*—Larson & Taylor PLC

(57) ABSTRACT

This invention provides a process for preparing 1,1,1,2,3,3,3-heptafluoropropane, which comprises reacting 2-trifluoromethyl-3,3,3-trifluoropropionic acid with fluorine gas. The process according to this invention produces 1,1,1,2,3,3,3-heptafluoropropane with high selectivity and is an industrially efficient and economical method.

8 Claims, No Drawings

PROCESS FOR PREPARING 1,1,1,2,3,3,3-HEPTAFLUOROPROPANE

FIELD OF THE INVENTION

The present invention relates to a process for preparing 1,1,1,2,3,3,3-heptafluoropropane, which is useful as aerosol propellants, refrigerants, blowing agents and fire extinguishants.

BACKGROUND OF THE INVENTION

Known methods for preparing 1,1,1,2,3,3,3-heptafluoropropane include, for example, a method comprising reacting hexafluoropropene with hydrofluoric acid in the presence of an antimony catalyst (Japanese Unexamined Patent Publication No. 24362/1996), and a method comprising reacting hexafluoropropene with hydrofluoric acid using a hydrogen fluoride adduct of an organic nitrogen base as a reaction medium (Japanese Unexamined Patent Publication No. 53543/1998).

Hexafluoropropene used as a starting material in these reactions is highly useful as a fluororesin monomer and as an intermediate for fluorochemicals, and is expensive. Therefore, the above methods have a cost disadvantage.

Perfluoroisobutene (hereinafter referred to as "PFIB") is a byproduct in the manufacture of hexafluoropropene. PFIB is a highly toxic compound which is usually converted to the less harmful methanol adduct. Effective uses of the PFIB-methanol adduct, however, are not generally known.

Japanese Unexamined Publication No. 309791/1995 describes a method for preparing hexafluoropropane, perfluoropropane and heptafluoropropane using PFIB as a starting material. The method comprises the steps of reacting PFIB-alkanol adducts (e.g., 2H-octafluoroisobutyl methyl ether and heptafluoroisobutenyl methyl ether) with trialkylamine and water to produce hexafluoropropane and electrolyzing and fluorinating hexafluoropropane to give perfluoropropane and heptafluoropropane. According to this method, only a small amount (about 10%) of heptafluoropropane is obtained as a byproduct.

WO 98/28247 describes a method for preparing heptafluoropropane, which comprises reacting hexafluoropropane with fluorine gas. This method also produces a large amount of byproducts, such as perfluoropropane.

U.S. Pat. No. 3,399,179 and J. Org. Chem., 34, 2446 (1969) describe a method of reacting carboxylic acid with fluorine gas to replace carboxyl groups with fluorine atoms. This method comprises bringing carboxylic acid or a metal salt thereof into contact with fluorine gas in the presence of a diluent such as water or alcohol to produce fluoride. However, it has been revealed that 2-trifluoromethyl-3,3,3-trifluoropropionate can not be fluorinated by this method.

SUMMARY OF THE INVENTION

An object of the present invention is to provide a process for preparing 1,1,1,2,3,3,3-heptafluoropropane with high selectivity in an industrially efficient and economical manner.

The inventors of the present invention carried out extensive research to develop a method for preparing heptafluoropropane using 2-trifluoromethyl-3,3,3-trifluoropropionic acid obtained from PFIB-methanol adducts (Japanese Unexamined Publication No. 325179/1996). The inventors found that when 2-trifluoromethyl-3,3,3-trifluoropropionic acid is reacted with fluorine gas, heptafluoropropane is obtained with high selectivity. The present invention has been accomplished based on this finding.

The present invention provides processes for preparing 1,1,1,2,3,3,3-heptafluoropropane as shown below.

1. A process for preparing 1,1,1,2,3,3,3-heptafluoropropane, which comprises reacting 2-trifluoromethyl-3,3,3-trifluoropropionic acid with fluorine gas.
2. The above process 1 wherein fluorine gas is diluted with a gas inert to fluorine gas.
3. The above process 2 wherein the gas inert to fluorine gas is at least one member selected from the group consisting of nitrogen, helium, anhydrous hydrogen fluoride, 1,1,1,2,3,3,3-heptafluoropropane and argon.
4. The above process 2 wherein the concentration of fluorine gas is 5 to 30 mol % in a mixed gas of fluorine gas and inert gas.
5. The above process 1 wherein a 50 or more mass % solution of 2-trifluoromethyl-3,3,3-trifluoropropionic acid is reacted with fluorine gas.
6. The above process 1 wherein 2-trifluoromethyl-3,3,3-trifluoropropionic acid is reacted with fluorine gas in the presence of a solvent inert to fluorine gas.
7. The above process 6 wherein the solvent inert to fluorine gas is at least one member selected from the group consisting of perfluoroalkanes, chlorotrifluoroethylene oligomeric oils, perfluoropolyether oils and anhydrous hydrogen fluoride.
8. The above process 1 wherein the reaction is carried out at a temperature of −20° C. to 100° C.

DETAILED DESCRIPTION OF THE INVENTION

According to the present invention, 2-trifluoromethyl-3,3-trifluoropropionic acid is brought into contact with fluorine gas to simultaneously undergo fluorination and decarboxylation, thus providing 1,1,1,2,3,3,3-heptafluoropropane.

It is preferable to use a high purity 2-trifluoromethyl-3,3-trifluoropropionic acid in the present invention. However, since high purity 2-trifluoromethyl-3,3,3-trifluoropropionic acid is solid at ordinary temperature (mp 49–50° C.), it tends to be difficult to handle in the reaction with fluorine gas. When a high purity 2-trifluoromethyl-3,3,3-trifluoropropionic acid is used, it is recommendable to use a reaction temperature slightly higher than room temperature so that 2-trifluoromethyl-3,3,3-trifluoropropionic acid becomes liquid and the reaction can proceed even in the absence of solvents.

Japanese Unexamined Publication No. 325179/1996 describes that 2-trifluoromethyl-3,3,3-trifluoropropionic acid can be prepared by reacting 2-trifluoromethyl-1,3,3,3-tetrafluoro-1-alkoxypropene with metal halide in the presence of water and a water soluble organic solvent and that the reaction product can be purified by separating the organic layer, followed by rectification. However, it is not easy for a simple distillation to completely separate 2-trifluoromethyl-3,3,3-trifluoropropionic acid from the water soluble organic solvent. The resulting 2-trifluoromethyl-3,3,3-trifluoropropionic acid usually contains 20 to 30 mol % of the water soluble organic solvent.

Such carboxylic acid can be purified by a method comprising neutralizing carboxylic acid with alkali to give an aqueous solution, washing the solution with an organic solvent such as dichloromethane to remove impurities and reacidifying the solution. However, such a process has a cost disadvantage.

According to the process for preparing 1,1,1,2,3,3,3-heptafluoropropane of the invention, the starting material 2-trifluoromethyl-3,3,3-trifluoropropionic acid may contain water soluble organic solvents such as acetonitrile, tetrahydrofuran and acetone. Also, the starting material 2-trifluoromethyl-3,3,3-trifluoropropionic acid may be dissolved in at least one solvent selected from water soluble organic solvents (e.g., acetonitrile, tetrahydrofuran and acetone) and water.

In this case, the amount of water soluble organic solvents and/or water is preferably 50 mass % or less, more preferably 20 mass % or less. In other words, it is preferable to react a 50 or more mass % solution of 2-trifluoromethyl-3,3,3-trifluoropropionic acid with fluorine gas. It is more desirable to use a 80 or more mass % solution of 2-trifluoromethyl-3,3,3-trifluoropropionic acid. A large amount of water soluble organic solvents and/or water not only causes low utilization efficiency of fluorine gas but also causes combustion reaction of water soluble organic solvents, thus being dangerous.

When the starting material 2-trifluoromethyl-3,3,3-trifluoropropionic acid contains water as an impurity, a highly corrosive hydrogen fluoride aqueous solution is formed from hydrogen fluoride generated by the reaction and the water, and corrodes the reaction vessel. Therefore, it is preferable for the starting material not to contain a substantial amount of water.

To increase safety, 2-trifluoromethyl-3,3,3-trifluoropropionic acid can be reacted with fluorine gas in the presence of a solvent inert to fluorine gas according to the present invention.

Examples of solvents inert to fluorine gas include perfluoroalkanes such as perfluorohexane and perfluorocyclobutane; fluorine oils such as chlorotrifluoroethylene oligomeric oils and perfluoropolyether oils; and anhydrous hydrogen fluoride.

In the case of using such solvents, it is preferable to react a 10 or more mass % solution of 2-trifluoromethyl-3,3,3-trifluoropropionic acid with fluorine gas. It is more desirable to use a 30 or more mass % solution of 2-trifluoromethyl-3,3,3-trifluoropropionic acid.

Fluorine gas is fed into the reaction system preferably as diluted with a gas inert to fluorine gas. Gas for dilution of fluorine gas can be selected from nitrogen, helium, argon, anhydrous hydrogen fluoride, 1,1,1,2,3,3,3-heptafluoropropane and the like, of which nitrogen is the most cost-effective.

It is preferable that the concentration of fluorine gas (fluorine gas concentration in a mixed gas of fluorine gas and inert gas) be 5 to 30 mol %. When the concentration of fluorine gas is too high, an explosive reaction is likely to proceed and becomes dangerous. On the other hand, when the concentration is too low, a large amount of inert gas is wasted and loss of 1,1,1,2,3,3,3-heptafluoropropane with the inert gas tends to occur.

The molar ratio of 2-trifluoromethyl-3,3,3-trifluoropropionic acid to fluorine gas is preferably 1:1 to 1:2, more preferably 1:1 to 1:1.5.

The reaction temperature is preferably −20° C. to 100° C., more preferably 0° C. to 30° C.

The reaction can be suitably carried out by a semi-continuous process comprising placing a mixture of the starting material 2-trifluoromethyl-3,3,3-trifluoropropionic acid and the solvent in a reaction vessel and continuously feeding fluorine gas (adding 2-trifluoromethyl-3,3,3-trifluoropropionic acid properly), or by a continuous process comprising placing a mixture of the starting material 2-trifluoromethyl-3,3,3-trifluoropropionic acid and the solvent in a reaction vessel and continuously feeding fluorine gas and 2-trifluoromethyl-3,3,3-trifluoropropionic acid.

For carrying out these reactions, it is suitable to use metal autoclaves. Alternatively, other reaction vessels can be used, such as contact packed towers, and there is no specific limitation.

The fluorine gas flow per hour is preferably about 0.1 to 10 times, more preferably about 0.5 to 5 times, the volume of the reaction vessel.

The reaction is preferably carried out usually at atmospheric pressure. In some cases, however, it may be carried out under reduced pressure or under a slight pressure.

According to the present invention, 1,1,1,2,3,3,3-heptafluoropropane can be obtained with high selectivity in an industrially efficient and economical manner.

BEST MODE FOR CARRYING OUT THE INVENTION

The following Examples illustrate the present invention in further detail.

EXAMPLE 1

A 200-ml SUS 316 reaction vessel was charged with 60 g (0.31 mole) of 2-trifluoromethyl-3,3,3-trifluoropropionic acid, which was then heated to 50° C. with stirring. Fluorine gas as diluted with nitrogen gas was fed into the liquid phase. The flow rate of fluorine gas was 10 ml/min, whereas the flow rate of nitrogen gas was 90 ml/min. The reaction was carried out at atmospheric pressure and the gas generated was washed with potassium sulfite-potassium hydroxide aqueous solution.

The gas thus obtained was analyzed by gas chromatography. The analysis confirmed formation of 1,1,1,2,3,3,3-heptafluoropropane, and showed that 1,1,1,2,3,3,3-heptafluoropropane was obtained with a selectivity of 100% in the gas. The liquid phase remaining in the reaction vessel was analyzed by $^{19}$F-NMR (Nuclear Magnetic Resonance). No peaks were observed except for those of the starting material.

EXAMPLE 2

A 200-ml SUS 316 reaction vessel was charged with 60 g of 94.2 mass % purity of 2-trifluoromethyl-3,3,3-trifluoropropionic acid (containing 5.8 mass % of acetonitrile as an impurity). While stirring 2-trifluoromethyl-3,3,3-trifluoropropionic acid at room temperature (25° C.), fluorine gas as diluted with nitrogen gas was fed into the liquid phase. The flow rate of fluorine gas was 10 ml/min, whereas the flow rate of nitrogen gas was 180 ml/min. The flow rate of nitrogen gas was gradually reduced to 40 ml/min so that the fluorine gas concentration became 20 mol %. The reaction was carried out at atmospheric pressure and the gas generated was washed with potassium sulfite-potassium hydroxide aqueous solution.

The gas thus obtained was analyzed by gas chromatography. The analysis confirmed formation of 1,1,1,2,3,3,3-heptafluoropropane, and showed that 1,1,1,2,3,3,3-heptafluoropropane was obtained with a selectivity of 100% in the gas (a trace amount of $NF^3$ was detected as a decomposition product of acetonitrile).

EXAMPLE 3

A 200-ml SUS 316 reaction vessel was charged with 60 g of 84.5 mass % purity of 2-trifluoromethyl-3,3,3- trifluoropropionic acid (containing 15.5 mass % of tetrahydrofuran as an impurity). While stirring 2-trifluoromethyl-3,3,3-trifluoropropionic acid at room temperature (25° C.), fluorine gas as diluted with nitrogen gas was fed into the liquid phase. The flow rate of fluorine gas was 10 ml/min, whereas the flow rate of nitrogen gas was 180 ml/min. The reaction was carried out at atmospheric pressure and the gas generated was washed with potassium sulfite-potassium hydroxide aqueous solution.

The gas thus obtained was analyzed by gas chromatography. The analysis confirmed formation of 1,1,1,2,3,3,3-heptafluoropropane, and showed that 1,1,1,2,3,3,3-heptafluoropropane was obtained with a selectivity of 100% in the gas.

EXAMPLE 4

A 200-ml SUS 316 reaction vessel was charged with 60 g of 2-trifluoromethyl-3,3,3-trifluoropropionic acid and 100 g of perfluorohexane, which was then cooled to 0° C. While stirring the mixture, 30 mol % fluorine gas (as diluted with nitrogen gas) was fed into the liquid phase at a flow rate of 100 ml/min. The reaction was carried out at atmospheric pressure and the gas generated was washed with potassium sulfite-potassium hydroxide aqueous solution.

The gas thus obtained was analyzed by gas chromatography. The analysis confirmed formation of 1,1,1,2,3,3,3-heptafluoropropane, and showed that 1,1,1,2,3,3,3-heptafluoropropane was obtained with a selectivity of 100% in the gas.

COMPARATIVE EXAMPLE 1

A 200-ml fluororesin (PFA) bottle was charged with 9.8 g of 2-trifluoromethyl-3,3,3-trifluoropropionic acid, 100 ml of water and 3.35 g of potassium hydroxide (KOH). While stirring the mixture at room temperature (25° C.), fluorine gas as diluted with nitrogen gas was fed into the liquid phase. The flow rate of fluorine gas was 10 ml/min, whereas the flow rate of nitrogen gas was 90 ml/min. The reaction was carried out at atmospheric pressure and the gas generated was washed with potassium sulfite-potassium hydroxide aqueous solution.

The gas thus obtained was analyzed by gas chromatography. Nothing other than nitrogen gas was detected.

What is claimed is:

1. A process for preparing 1,1,1,2,3,3,3-heptafluoropropane, which comprises reacting 2-trifluoromethyl-3,3,3-trifluoropropionic acid with fluorine gas.

2. The process according to claim 1 wherein fluorine gas is diluted with a gas inert to fluorine gas.

3. The process according to claim 2 wherein the gas inert to fluorine gas is at least one member selected from the group consisting of nitrogen, helium, anhydrous hydrogen fluoride, 1,1,1,2,3,3,3-heptafluoropropane and argon.

4. The process according to claim 2 wherein the concentration of fluorine gas is 5 to 30 mol % in a mixed gas of fluorine gas and inert gas.

5. The process according to claim 1 wherein a 50 or more mass % solution of 2-trifluoromethyl-3,3,3-trifluoropropionic acid is reacted with fluorine gas.

6. The process according to claim 1 wherein 2-trifluoromethyl-3,3,3-trifluoropropionic acid is reacted with fluorine gas in the presence of a solvent inert to fluorine gas.

7. The process according to claim 6 wherein the solvent inert to fluorine gas is at least one member selected from the group consisting of perfluoroalkanes, chlorotrifluoroethylene oligomeric oils, perfluoropolyether oils and anhydrous hydrogen fluoride.

8. The process according to claim 1 wherein the reaction is carried out at a temperature of −20° C. to 100° C.

* * * * *